(12) United States Patent
Camp

(10) Patent No.: US 11,667,728 B1
(45) Date of Patent: Jun. 6, 2023

(54) REACTOR AND PROCESSES FOR ENDOTHERMIC REACTIONS AT HIGH TEMPERATURES

(71) Applicant: David T. Camp, Midland, MI (US)

(72) Inventor: David T. Camp, Midland, MI (US)

(*) Notice: Subject to any disclaimer, the term of this patent is extended or adjusted under 35 U.S.C. 154(b) by 0 days.

(21) Appl. No.: 17/887,792

(22) Filed: Aug. 15, 2022

Related U.S. Application Data

(60) Provisional application No. 63/315,808, filed on Mar. 2, 2022.

(51) Int. Cl.
| | |
|---|---|
| *C08F 2/01* | (2006.01) |
| *B01J 19/20* | (2006.01) |
| *C08F 12/08* | (2006.01) |
| *B01J 19/24* | (2006.01) |
| *C07C 5/333* | (2006.01) |

(52) U.S. Cl.
CPC ............... *C08F 2/01* (2013.01); *B01J 19/20* (2013.01); *C08F 12/08* (2013.01); *B01J 2219/00157* (2013.01)

(58) Field of Classification Search
USPC .......................................... 585/440; 422/228
See application file for complete search history.

(56) References Cited

U.S. PATENT DOCUMENTS

| | | | |
|---|---|---|---|
| 3,702,346 A * | 11/1972 | Kellar | ................... C07C 5/327 585/440 |
| 4,716,023 A | 12/1987 | Christner et al. | |
| 4,911,894 A | 3/1990 | Retallick et al. | |
| 5,651,800 A | 7/1997 | Mizuno et al. | |
| 6,380,449 B1 * | 4/2002 | Butler | ................... C07C 5/333 585/443 |
| 6,835,360 B2 | 12/2004 | Warren | |
| 7,132,555 B2 | 11/2006 | Te Raa et al. | |
| 7,500,999 B2 | 3/2009 | Aaron et al. | |
| 8,021,447 B2 | 9/2011 | Popham et al. | |
| 9,556,025 B2 | 1/2017 | Krueger et al. | |
| 10,954,152 B1 * | 3/2021 | Hicks | ................... B01J 19/002 |
| 2003/0180201 A1 | 9/2003 | Belt et al. | |

(Continued)

FOREIGN PATENT DOCUMENTS

| | | |
|---|---|---|
| DE | 2213385 A1 | 10/1973 |
| FR | 2780316 A1 | 12/1999 |
| WO | 2008068156 A1 | 6/2008 |

*Primary Examiner* — Fred M Teskin
(74) *Attorney, Agent, or Firm* — Dentons Cohen & Grigsby P.C.

(57) ABSTRACT

An endothermic catalytic reactor apparatus that includes a radiant furnace that includes a burner adapted to provide thermal energy to the furnace, a reactor that includes an entrance portion and an exit portion and is situated within the furnace and adapted to receive radiant thermal energy. The reactor includes one or more static helical spirals defining a flow path within the reactor that travels from the entrance portion to the exit portion. The helical spirals are adapted to hold a catalyst on an outer surface thereof. Incoming port(s) are located on the entrance portion and are adapted to receive reactive starting materials. An exit port is located near the exit portion and is adapted to expel product from the reactor. The reactor is adapted to allow starting materials to receive radiant thermal energy and interact with catalyst sufficiently to cause a reaction to occur that converts starting materials to product.

18 Claims, 2 Drawing Sheets

(56) References Cited

U.S. PATENT DOCUMENTS

2008/0269431 A1  10/2008  Sarcinelli et al.
2009/0253005 A1  10/2009  Muehlner et al.
2020/0021010 A1   1/2020  Ou et al.

\* cited by examiner

REACTOR AND PROCESSES FOR ENDOTHERMIC REACTIONS AT HIGH TEMPERATURES

CROSS-REFERENCE TO RELATED APPLICATIONS

This application claims the benefit of U.S. Provisional Application No. 63/315,808 filed on Mar. 2, 2022, which is hereby incorporated by reference in its entirety.

TECHNICAL FIELD

The present disclosure is directed to an endothermic catalytic reactor apparatus that includes a furnace and a reactor.

BACKGROUND

An endothermic process is any process with an increase in the enthalpy or internal energy of a system. In such a process, a closed system usually absorbs thermal energy from its surroundings, which can be heat transfer into the system. For example, if more energy is needed to break bonds than the energy being released, energy is taken up, and an endothermic reaction results.

SUMMARY

The present disclosure provides an endothermic catalytic reactor apparatus that includes a radiant furnace and an endothermic reactor. The radiant furnace includes a burner adapted to provide thermal energy to the furnace. The reactor has an entrance portion and an exit portion and is situated within the furnace and adapted to receive radiant thermal energy from the furnace. The reactor includes one or more static helical spirals defining a flow path within the reactor so that a material can follow the defined flow path to travel from the entrance portion to the exit portion. The helical spirals are adapted to hold a catalyst on an outer surface thereof. One or more incoming ports are located on the entrance portion and are adapted to receive reactive starting materials. An exit port is located on or near the exit portion and is adapted to expel product from the reactor. The reactor is adapted to allow the starting materials to receive radiant thermal energy and interact with the catalyst sufficiently to cause a reaction to occur that converts starting materials to product.

DETAILED DESCRIPTION

Figure 1:
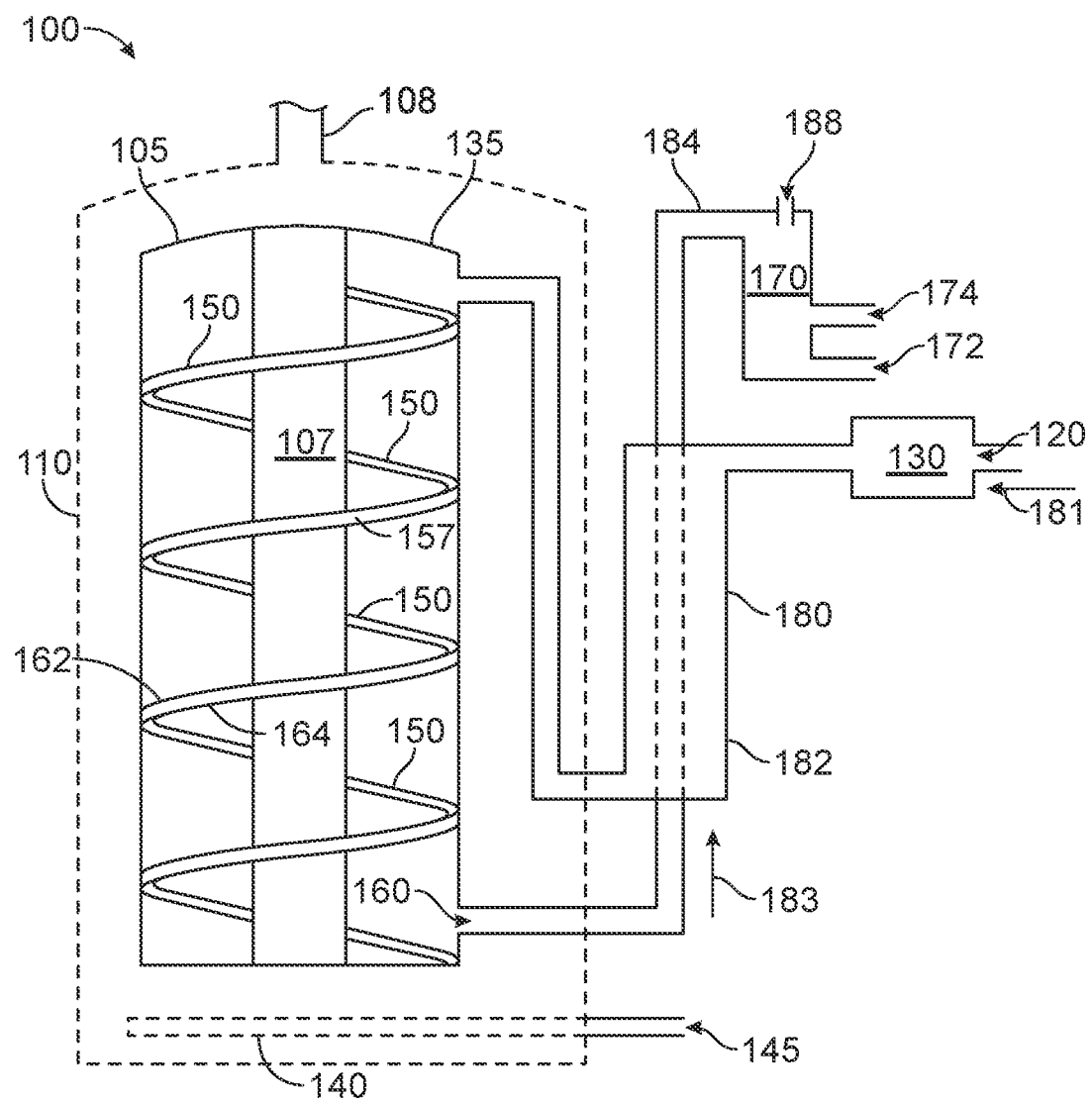
FIG. 1 is a front elevation view schematic of a reactor apparatus according to this disclosure.
Figure 2:
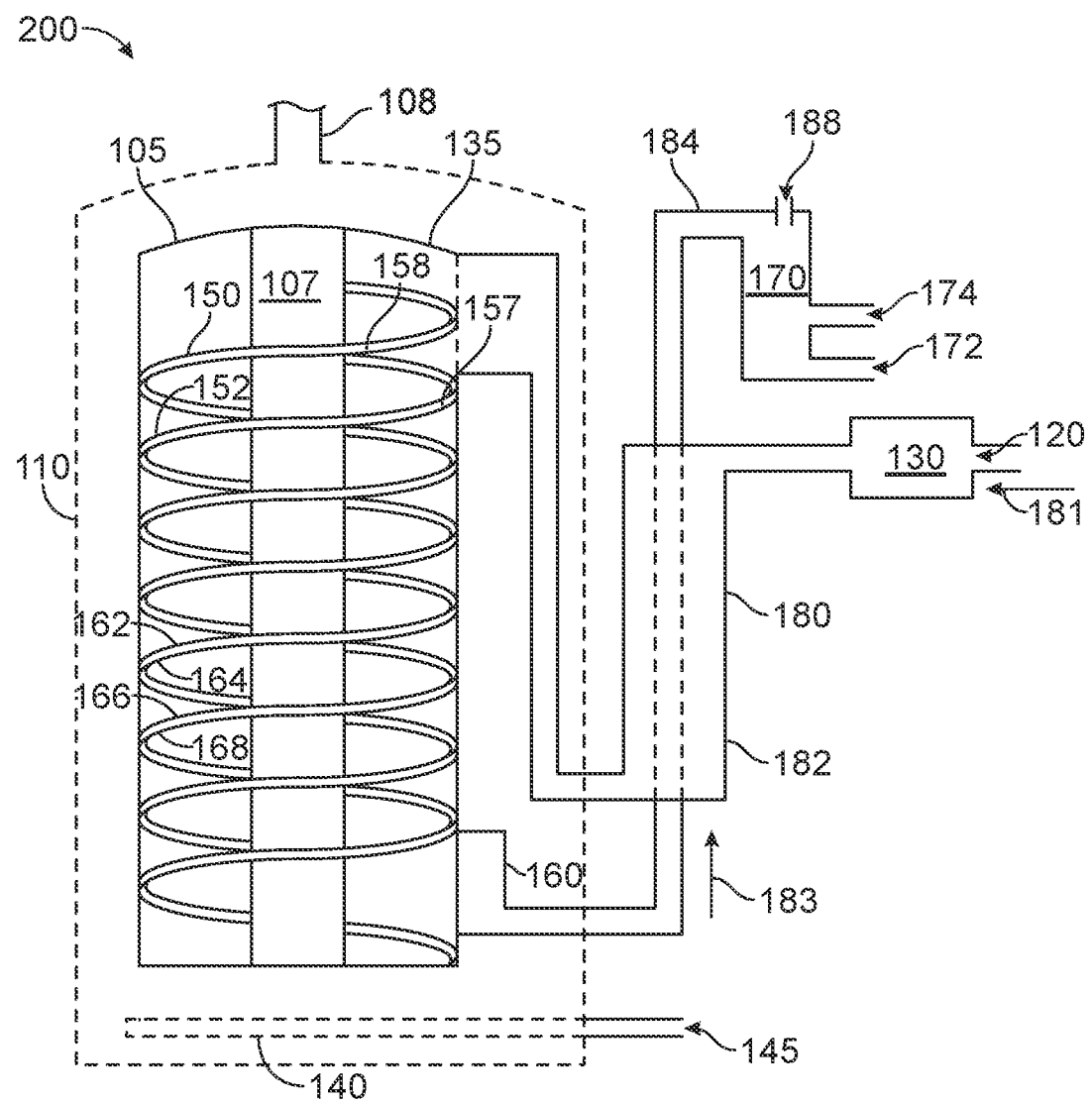
FIG. 2 is a front elevation view schematic of a reactor apparatus according to this disclosure.

It is to be understood that this disclosure may assume various alternative variations and step sequences, except where expressly specified to the contrary. As a nonlimiting example, FIGS. 1 and 2 show the axis of reactor 105 in a vertical position and the reactant flow proceeding downward, but this is not a requirement. The axis of reactor 105 can be vertical, horizontal or any orientation appropriate for implementation. Accordingly, unless indicated to the contrary, the numerical parameters set forth in the following specification and attached claims are approximations that can vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

All ranges are inclusive and combinable. For example, the term "a range of from 0.06 to 0.25 wt. %, or from 0.06 to 0.08 wt. %" would include each of from 0.06 to 0.25 wt. %, from 0.06 to 0.08 wt. %, and from 0.08 to 0.25 wt. %. Further, when ranges are given, any endpoints of those ranges and/or numbers recited within those ranges can be combined within the scope of the present disclosure.

As used herein, unless otherwise expressly specified, all numbers such as those expressing values, ranges, amounts or percentages can be read as if prefaced by the word "about", even if the term does not expressly appear. Unless otherwise stated, plural encompasses singular and vice versa. As used herein, the term "including" and like terms means "including but not limited to".

As used herein, the transitional term "comprising" (and other comparable terms, e.g., "containing" and "including") is "open-ended" and open to the inclusion of unspecified matter. Although described in terms of "comprising", the terms "consisting essentially of" and "consisting of" are also within the scope of the disclosure.

As used herein, the articles "a", "an", and "the" include plural references unless expressly and unequivocally limited to one referent.

As used herein, the term "defined path" refers to the spiral pathway(s) through a reactor defined the surfaces of the helical spiral(s) and the distance from the inner side of the wall of the reactor and the outer surface of an optional central shaft extending along the central axis of the reactor.

As used herein, the term "endothermic reactor" refers to a reactor adapted to allow a chemical reaction to take place that absorbs thermal energy or heat from its environment. The absorbed energy provides the activation energy for the chemical reaction to occur.

As used herein, the term "helical spiral" refers to a spiral blade that can be coiled around a shaft. While a central shaft can be used to construct and maintain the helical spiral, it is not required for the process. The coiling simply needs to be such that there is no center hole for the process stream to short-circuit.

As used herein, the term "linear velocity" refers to the distance a gas will travel in a given time.

As used herein, the term "mass flow rate" refers to the mass of a liquid substance passing per unit of time. SI units are kilogram per second. The mass flow directly depends on the density, velocity of the liquid, and the area of the cross-section. Mass flow rate can be determined according to the equation:

$$m = \rho V A$$

where, $\rho$=density of fluid, V=velocity of liquid, and A=cross sectional area.

As used herein, the term "Nusselt number" refers to the ratio of convective to conductive heat transfer at a boundary in a fluid. A Nusselt number of value one represents heat transfer by pure conduction. A value between one and 10 is characteristic of laminar flow. A larger Nusselt number corresponds to more active convection, with turbulent flow typically in the 100-1000 range.

As used herein, the term "radiant furnace" refers to as a direct heater or a direct fired heater used to provide thermal energy or heat for a reactor. They are used to provide heat for a process. The radiant furnace design can vary as to its type of fuel and method of introducing combustion air. Heat is generated by mixing fuel with air or oxygen, or from electrical energy. The residual heat can exit the furnace as flue gas.

As used herein, the term "Reynolds number" refers to the dimensionless ratio of inertial forces to viscous forces within a fluid which is subjected to relative internal movement due to different fluid velocities. The Reynolds number helps predict flow patterns in different fluid flow situations. At low Reynolds numbers, flows tend to be dominated by laminar flow, while at high Reynolds numbers flows tend to be turbulent. When the Reynolds number is less than about 2,000, flow in a pipe is generally laminar, whereas, at values greater than 3,000, flow is usually turbulent.

As used herein, the term "volumetric flow rate" refers to the fluid volume that passes a specified point per unit of time. Volumetric flow rate can be determined according to the equation:

$$Q = AV$$

where Q is the volume flow rate, A is the cross-sectional area occupied by the flowing material, and V is the average velocity of flow.

Disclosed herein is an endothermic catalytic reactor apparatus that includes a radiant furnace and a reactor. The radiant furnace includes a burner adapted to provide thermal energy to the furnace. The reactor has a reactant entrance and an exit, is situated within the furnace and adapted to receive radiant thermal energy from the furnace. Within the reactor are one or more static helical spirals positioned within the reactor so that a material can follow a defined path to travel from the reactant entrance to the exit. The helical spirals are adapted to hold a catalyst on an outer surface thereof. One or more incoming ports are located on the entrance portion of the reactor and are adapted to receive reactive starting materials. The reactor includes one or more exit ports on or near an exit portion, which are adapted to expel product from the reactor. The reactor is adapted to allow the starting materials to receive radiant thermal energy and interact with the catalyst sufficiently to cause a reaction to occur that converts starting materials to product.

As shown in FIG. 1, reactor apparatus 100 includes endothermic reactor 105 and radiant furnace 110 (in dashed lines), which includes flue 108. Reactants are provided to endothermic reactor 105 through reactant feed line 120 and can be optionally heated by flowing through optional heat exchanger 130 and optional heat exchanger 180 and subsequently emptying into endothermic reactor 105 at the entrance portion 135 of reactor 105 (heat exchangers 130 and 180 are optional and can be utilized depending on the process to be carried out in reactor 105). As shown, reactant feed line 120 travels through shell side 182 of heat exchanger 180 and material travels in the direction of arrow 183. Radiant furnace 110 encases substantially all of endothermic reactor 105 and includes burner 140 (shown with dashed lines) which can combust a flammable material from line 145 or, alternatively, be an electric heating element within radiant furnace 110.

Endothermic reactor 105 includes static helical spiral 150 that includes a defined path positioned within endothermic reactor 105 around central shaft 107 and adapted to allow reactants to follow the defined path to travel from entrance portion 135 to product discharge 160. Helical spiral 150 has a thickness 157 described herein. Helical spiral 150 can be adapted to contain a catalyst on an outer surface thereof, first surface 162 and second surface 164. Radiant furnace 105 provides sufficient thermal energy to allow reactants to be converted to product either through direct conversion or catalyzed reaction through interaction with the catalyst contained on the first and second surfaces 162 and 164 of helical spiral 150. The effluent from product discharge 160 passes through tube 184 of heat exchanger 180 in the direction of arrow 183, heating the contents of reactants in shell side 182. Reactants can be sufficiently heated to be in a gaseous or vapor state leaving heat exchanger 130 and heated to near reaction temperature when leaving heat exchanger 180 and entering endothermic reactor 105.

The flows through heat exchanger 180 can be countercurrent as shown in FIG. 1 where reactants flow through reactant feed line 120 in a direction shown as first flow direction 181 and a product stream flows through product discharge line 160 in a direction shown as second flow direction 182.

Catalysts can be employed as described herein to increase the reaction rate of the process in reactor 105. The catalysts may not change the maximum conversion at a given temperature. In some cases, given the efficient energy transport accompanying the highly turbulent helical reactant flow and the elevated temperatures achievable with radiant furnace 110, direct conversion, such as acceptable process performance can be obtained without a catalyst.

The product leaving tube 184 of heat exchanger 180 can be separated in separator 170 which can produce several separated streams shown as nonlimiting exemplary streams 172, 174 and overhead stream 188. One of streams 172 and 174 may be a primarily organic stream and the other may be an aqueous stream. Non-condensable materials can be removed in separator 170 via overhead stream 188. When the non-condensable materials are flammable material, they can be used in in burner 140 when it is a combustion burner after either being mixed with other flammable materials or used alone in line 145.

As shown in FIG. 2, where features in FIG. 1 that are similar are numbered the same, reactor apparatus 200 includes endothermic reactor 105 and radiant furnace 110 (in dashed lines), which includes flue 108. Reactants are provided to endothermic reactor 105 through reactant feed line 120 and can be optionally heated by flowing through heat exchanger 130 and optional heat exchanger 180 and subsequently emptying into endothermic reactor 105 at the entrance portion 135 of reactor 105. As shown, reactant feed line travels through shell side 182 of heat exchanger 180 and material travels in the direction of arrow 183. Radiant furnace 110 encases substantially all of endothermic reactor 105 and includes burner 140 (shown with dashed lines)

which can combust a flammable material or, alternatively, be an electric heating element within radiant furnace 110.

Endothermic reactor 105 includes first static helical spiral 150 and second helical spiral 152, which can be positioned within endothermic reactor 105 around central shaft 107 and adapted to allow reactants to follow a defined path to travel from entrance portion 135 to product discharge 160. The helical spirals 150 and 152 can have a thickness 158 and 157 respectively described herein. The defined path can be adapted to contain a catalyst on an outer surface thereof, first and third surfaces 162 and 166 and second and fourth surfaces 164 and 168 respectively. Radiant furnace 105 provides sufficient thermal energy to allow reactants to be converted to product either through direct conversion or catalyzed reaction through interaction with the catalyst contained on first, second, third and fourth surfaces 162, 164, 166 and 168 of helical spirals 150 and 152. The effluent from product discharge 160 passes through tube 184 of heat exchanger 180 in the direction of arrow 183, heating the contents of reactants in shell side 182. Reactants can be sufficiently heated to be in a gaseous or vapor state leaving heat exchanger 130 and heated to near reaction temperature when leaving heat exchanger 180 and entering endothermic reactor 105.

The flows through heat exchanger 180 can be countercurrent as shown in FIG. 1 where reactants flow through reactant feed line 120 in a direction shown as first flow direction 181 and a product stream flows through product discharge line 160 in a direction shown as second flow direction 182.

The product leaving tube 184 of heat exchanger 180 can be separated in separator 170 which can produce several separated streams shown as nonlimiting exemplary streams 172, 174 and overhead stream 188. One of streams 172 and 174 may be a primarily organic stream and the other may be a primarily aqueous stream. Non-condensable materials can be removed in separator 170 via overhead stream 188. When the non-condensable materials are flammable material, they can be used in in burner 140 when it is a combustion burner after either being mixed with other flammable materials or used alone in line 145.

As shown in FIGS. 1 and 2, the spiral flow along the defined path and against the reactor wall at high velocity can provide excellent energy transfer between the reactor wall and reactants regardless of reactor orientation (vertical, horizontal or sloped). This wall-to-reactant transfer can be so efficient that the overall transfer between the radiant furnace and reactants may be limited only by the thermal conductivity and thickness of the reactor wall.

The starting materials can pass through a heat exchanger prior to entering reactor 105 so they enter reactor 105 in a gaseous or vapor state at a temperature of from 225° C., such as 275° C., 325° C. or 425° C. and can be up to 725° C., such as 675° C. or 625° C. The temperature of the starting materials entering reactor 105 can be any value or range between any of the values recited above.

The starting materials can be mixed with super-heated steam prior to entering reactor 105 in order to aid in achieving desired temperatures and flow properties while traversing the defined flow path through reactor 105.

The dimensions of endothermic reactor 105, the defined path through endothermic reactor 105 and the flow rate of reactants, or starting materials, into reactor 105 and the flow rate of product out of reactor 105 can be tailored to the specific process to be employed therein. As a nonlimiting example, reactant feed line 120 can empty into reactor 105 through a port that can have any suitable cross-sectional shape, nonlimiting examples being circular, oval, square, rectangular or parallelogram. Other suitable shapes of reactor 105 include a barrel shape or an hour-glass shape. The cross-sectional area of the port can be at least 0.5 m$^2$, such as 1 m$^2$ or 2 m$^2$ and can be up to 6 m$^2$, such as 5 m$^2$ or 4 m$^2$. The cross-sectional area of the port for starting materials entering reactor 105 can be any value or range between any of the values recited above.

Reactor 105 can be cylindrical and enclosed at both ends. As indicated, reactor 105 can include a static helical spiral as shown in FIG. 1 or a static helical spiral with multiple parallel spirals, as shown in FIG. 2 with two parallel spirals. There are ports at each end to receive and discharge the reactant stream. The spirals can extend from an optional central spine to the generally cylindrical wall. The wall can be made of metal with high thermal conductivity and the minimal thickness required for stability at the reaction temperature. Reactor 105 is adapted to allow the starting materials to receive radiant thermal energy and interact with the catalyst sufficiently to cause a reaction to occur that converts starting materials to product. The helical spiral—reactor wall combinations can allow reactant flow at high velocities, i.e., turbulent, against the reactor wall, which can affect the energy transport between the wall and the reactant stream.

The inner diameter of reactor 105 and can be selected based on the specific process to be employed therein. The reactor diameter can be at least 1 m, such as 3 m or 4 m and can be up to 10 m, such as 7 m or 4 m. The diameter of reactor 105 can be any value or range between any of the values recited above.

With many shapes for reactor 105, the reactor walls can be tapered, which can reduce leakage where the edge of the spiral meets the wall. This configuration is similar to a fitted tapered stopper and reduces leakage compared to one with straight sides.

When reactor 105 is barrel or an hour-glass shape, the spiral helix can be built first and then reactor walls can be wrapped "mummy-fashion" around the spiral helix.

The single spiral shown in FIG. 1 can alternatively be accomplished without central shaft 107. This alternative approach can be used when the width of the helical surface is wide enough to cover the reactor diameter, thus avoiding a short circuit along the central axis.

The helical spirals, shown as 150 and 152 in FIGS. 1 and 2 can make any suitable number of revolutions so long as they originate at reactant feed line 120, which provides reactants or starting materials to reactor 105 and terminate at product discharge 160. The helical spirals can make at least 1.5, such as 2 or 2.5 revolutions and can make up to 6.5, such as 5.5, 5, or 4.5 revolutions. The number of revolutions of the helical spirals can be any value or range between any of the values recited above. As those skilled in the art can appreciate, a 0.5 revolution places reactant feed line 120 and product discharge 160 on the same side of reactor 105, while a full revolution placed reactant feed line 120 and product discharge 160 on opposite sides of reactor 105. The number of revolutions of the helical spirals will depend on the process to be employed and the position and orientation of reactor 105 and associated equipment.

The width of the helical spirals 150 and 152 can be the same, or nearly the same as the inner diameter of reactor 105 such that there is a sufficient fit between the spiral edge and the wall of reactor 105 so that leakage of reactants or starting materials from the desired helical flow (defined path) is minimized.

The pitch of helical spirals, shown as 150 and 152 in FIGS. 1 and 2, can be whatever pitch allows the helical spirals to traverse from the reactant feed line 120 provides reactants or starting materials to reactor 105 and to product discharge 160 and can be selected based on the specific process to be employed therein. The pitch of the helical spirals can be at least 0.25 m, such as 0.5 m or 0.75 m and can be up to 5 m, such as 4 m, 3 m or 2 m. The pitch of the helical spirals can be any value or range between any of the values recited above.

Reactor 105, helical spirals 150 and 152 and the other components of reactor apparatus 100 and reactor apparatus 200 can be constructed of any material that will be stable in the presence of the process to be performed therein, not degrade due to the temperatures and pressures employed. Nonlimiting examples of suitable materials of construction include 304 stainless steel, 316 stainless steel, 316L stainless steel, copper, aluminum, Alloy A-286, Alloy 20, Alloy 230, Alloy 400, Alloy 600, Alloy 625, Alloy B-2, Alloy B-3, Alloy C-276, Nickel 200, Titanium Grades 2, 3, 4, and 7, Zirconium 702, Zirconium 705 and combinations thereof. The walls of reactor 105 can be made from a material of suitably high thermal conductivity, such as copper or aluminum such that the walls readily transfer thermal energy or heat from the furnace to the contents of reactor 105.

As indicated above, the one or more helical spirals, shown as 150 in FIGS. 1 and 150 and 152 in FIG. 2, can be adapted to contain a catalyst on an outer surface thereof, shown as upper sides 162 and 166 and under sides 164 and 168 respectively. The particular catalyst will vary depending on the process to be performed in reactor 105. As nonlimiting examples, the catalyst can be deposited on the outer surface and thermally aged; embedding catalyst containing nanoparticles on the outer surface through a redox reaction at a solid-solution interface; embedding the catalyst in an abraded, perforated, or stiff mesh material installed on the outer surface; supporting a catalyst on a stable support material with a high specific surface area, nonlimiting examples including alumina, silica, zeolite, and carbon, which enables the high specific surface area of the catalyst to be maintained with high catalytic activity; and other methods known in the art. Regardless of how the catalyst is held to the outer surface, the catalyst will be separate from and not impede the defined flow path so that high volumes and high flow rates, as described above, can be maintained.

The thickness of the helical spirals, shown as 157 in FIGS. 1 and 2, can be any thickness that provides sufficient structural integrity to the helical spiral in the desired process, but not so thick as to impede heat transfer or the defined flow path. As a nonlimiting example, the thickness of the helical spirals can be 0.3 cm, such as 1 cm or 2 cm and can be up to 5 cm, such as 4 cm. The thickness of the helical spirals can be any value or range between any of the values recited above.

Reactor 105 can include multiple helical spirals as shown in FIG. 2, where two helical spirals 150 and 152 are shown. When multiple helical spirals are employed, the spacing between one helical spiral and the nearest helical spiral will often be equidistant to provide the most efficient flow along the defined path. The spacing between helical spirals can vary from equidistant, however flow efficiency may be decreased as a result.

As shown in FIG. 2, product discharge 160 provides a path for an exit stream from both of the two parallel spirals 150 and 152, where both discharge into product discharge 160 in order to exit reactor 105.

The starting materials or reactants can optionally include steam to achieve desired physical parameters as described below. The ratio of steam to starting materials or reactants can be at least 0.25:1, such as 0.5:1 or 0.75:1 and can be up to 4:1, such as 3:1, 2:1 or 1.5:1. The ratio of steam to starting materials or reactants can be any value or range between any of the values recited above.

The pressure in reactor 105 can be any pressure that facilitates the flow or starting materials or reactants along the defined path and encourages conversion or reactants to product. The pressure in reactor 105 can be at least 0.25 atm, such as 0.5 atm or 0.75 atm and can be up to 10 atm, such as 8 atm, 6 atm, 4 atm or 2 atm. Appropriate valves and compressors as are known to those skilled in the art can be employed to achieve and regulate a desired pressure. The pressure in reactor 105 can be any value or range between any of the values recited above.

The starting materials and optional steam can have a mass flow rate through reactor 105 of from 20 kg/sec, such as 25 kg/sec or 30 kg/sec and can be up to 150 kg/sec, such as 140 kg/sec or 125 kg/sec. The mass flow rate for the starting materials and optional steam flowing through reactor 105 can be any value or range between any of the values recited above.

The starting materials and optional steam can have a volumetric flow rate through reactor 105 of from 500 l/sec, such as 600 l/sec or 700 l/sec and can be up to 1,000 l/sec, such as 900 l/sec or 500 l/sec. The volumetric flow rate for the starting materials and optional steam flowing through reactor 105 can be any value or range between any of the values recited above.

The starting materials and optional steam can have a linear velocity through reactor 105 of from 15 m/sec, such as 20 m/sec or 25 m/sec and can be up to 35 m/sec, such as 33 m/sec or 30 m/sec. The linear velocity for the starting materials and optional steam flowing through reactor 105 can be any value or range between any of the values recited above.

The dimensions of the defined path through endothermic reactor 105 and the flow rate of reactants, or starting materials, into reactor 105 and the flow rate of product out of reactor 105 are designed to achieve particular flow parameters. As a nonlimiting example, the starting materials are gaseous when entering reactor 105 and flow along the defined path such that the starting materials have a Reynolds number of from 1,000,000, such as 2,000,000 or 3,000,000 and up to 15,000,000, such as 12,500,000 or 10,000,000. The Reynolds number for the starting materials flowing through reactor 105 can be any value or range between any of the values recited above.

As a nonlimiting example, the starting materials are gaseous when entering reactor 105 and flow along the defined path such that the starting materials have a Nusselt number of from 3,000, such as 4,000 or 5,000 and can be up to 15,000, such as 12,500 or 10,000. The Nusselt number for the starting materials flowing through reactor 105 can be any value or range between any of the values recited above.

The radiant furnace 110 included in reactor apparatus 100 and reactor apparatus 200 can generate any suitable temperature for the process to be employed therein, which can include a temperature of from 350° C., such as 400° C. or 450° C. and can be up to 900° C., such as 850° C., 800° C. or 750° C. The radiant furnace temperature can be any value or range between any of the values recited above.

As indicated above, the starting materials can be gaseous when entering reactor 105 and flow along the defined path. The thermal energy or heat from the furnace can be readily transferred to the contents of reactor 105 and the high flow rates, as indicated by the Reynolds number and Nusselt number, provide sufficient and constant turnover at the catalytic surface of the helical spirals to allow starting materials to be converted to product.

The conversion of starting materials to product in reactor 105 will vary depending on the process and process conditions employed and can be at least 10%, such as 25%, 40%, 50%, 60%, 70%, 75% or 80% and can be up to 100%, such as, 99%, 95% or 90%. The conversion of starting materials to product can be any value or range between any of the values recited above.

An exit stream that includes product and optionally unreacted starting materials, optionally non-condensable materials and optional steam exits reactor 105 via line 160 and can enter heat exchanger 180. For ease of description, heat exchanger 180 is shown in a vertical orientation in FIGS. 1 and 2, roughly parallel with reactor 105. Especially in high volume applications, heat exchanger 180 can be in a horizontal orientation. The exit stream can be directed to tube side 184 of heat exchanger 180 flowing in the direction of arrow 183, where it can be used to heat starting materials or reactants transported from reactant feed line 120 to shell side 182 of heat exchanger prior to entering entrance portion 135 of reactor 105. The relative flow patterns in shell side 182 and tube side 184 can be in the same direction or in opposite or countercurrent directions depending on the process employed. The exit stream leaves tube 184 of heat exchanger 180 and enters separator 170. Separator 170 separates the exit stream into several separated streams shown as nonlimiting exemplary streams 172, 174 and overhead stream 188. One of streams 172 and 174 contain a primarily organic stream and the other a primarily aqueous stream. Non-condensable materials can be removed in separator 170 via overhead stream 188. When the non-condensable materials are flammable, they can be used in in burner 140 when it is a combustion burner after either being mixed with other flammable materials or used alone in line 145.

Conventional methods, such as distillation towers, can be used to isolate unreacted starting materials or reactants from product in the primarily organic stream and any unreacted starting materials or reactants from water in the primarily aqueous stream. The product can then be packaged as appropriate, the unreacted starting materials or reactants can be returned to reactant feed line 120 and the water can be regenerated into steam or super-heated steam and used as described above.

Thus, the present disclosure provides a method of converting reactants to product that includes passing reactants through a heat exchanger to provide heated reactants, that can be in a gaseous or vapor state and optionally include super-heated steam as described above at the temperatures described above; providing heated reactants to the endothermic catalytic reactor apparatus described above that can include a radiant furnace, as described above, that includes a burner, as described above, and adapted to provide thermal energy or heat to the furnace; a reactor, having any of the configurations described above, having a reactant feed line and a product discharge, situated within the furnace and adapted to receive radiant thermal energy or heat from the furnace; one or more static helical spirals adapted to hold catalyst as described above, positioned within the reactor so that material can follow a defined path from the reactor feed line to the product discharge; one or more incoming ports on the entrance portion, adapted to receive the reactants from the reactant feed line; and a product discharge port on or near the exit portion, adapted to expel product from the reactor; where the reactor is adapted to allow the reactants to receive radiant thermal energy and interact with the catalyst sufficiently to cause a reaction to occur that converts reactants to a product; and where the endothermic catalytic reactor apparatus is optionally adapted to isolate the optional one or more second flammable materials from a reaction taking place within the reactor and providing the optional one or more second flammable materials to the burner, as described above; and separating the product from non-product materials as described above.

As will be apparent to those skilled in the art, the endothermic catalytic reactor apparatus described herein can be used for a number of endothermic processes, nonlimiting examples being cracking alkanes, the reaction of thionyl chloride with cobalt(II) sulfate heptahydrate, and thermal decomposition reactions. Nonlimiting specific examples also include conversion of ethane to ethylene, propane to propylene, ethyl benzene to styrene, ethyl toluene to vinyl toluene, and diethyl benzene to divinyl benzene.

As a nonlimiting detailed example, the present disclosure provides a method of producing styrene that includes passing a reactant stream that includes ethyl benzene and optionally super-heated steam through a heat exchanger to provide a heated reactant stream as described above at a temperature of from 450° C., such as 475° C. or 525° C. and up to 725° C., such as 675° C. or 625° C.; providing the reactant stream to an endothermic catalytic reactor apparatus as described above that includes a radiant furnace as described above that includes a burner as described above adapted to provide thermal energy to the furnace; a reactor, having any of the configurations described above, having a reactant feed line and a product discharge, situated within the furnace and adapted to receive radiant thermal energy or heat from the furnace; one or more static helical spirals as described above that include a defined path positioned within the reactor so that a material can follow the defined path to travel from the reactant feed line to the product discharge, where the helical spirals are adapted to hold a catalyst on an outer surface thereof as described above; one or more incoming ports on the entrance portion, adapted to receive the heated reactants; and a product discharge on or near the exit portion, adapted to expel a product stream that includes styrene from the reactor; where the reactor is adapted to allow the heated reactant stream to receive radiant thermal energy and interact with the catalyst sufficiently to cause a reaction to occur that converts ethyl benzene to styrene and byproduct hydrogen; where the product stream incudes styrene, hydrogen, optionally unreacted ethyl benzene and optionally steam; separating the product stream into a primarily aqueous phase, a primarily organic phase and a non-condensable overhead that includes hydrogen; separating styrene from the primarily organic phase as described above and optionally the primarily aqueous phase as described above.

As indicated above, the wall-to-reactant transfer can be so efficient that the overall transfer between the radiant furnace and reactants may only be limited by the thermal conductivity and thickness of the reactor wall.

The conversion of ethyl benzene to styrene can be at least 70%, such as 75% or 80% and can be up to 100%, such as, 99%, 95% or 90%. The conversion of ethyl benzene to styrene can be any value or range between any of the values recited above.

As described above, styrene can be subsequently separated from the product stream.

The non-condensable hydrogen byproduct can be packaged using methods known in the art for subsequent uses, a nonlimiting example being use in electric vehicles, fuel cells, batteries or to generate electrical energy that could be used to supply the energy needed when burner 140 is electric. As another alternative, the hydrogen could be used as flammable material in line 145 when burner 140 is a combustion burner.

As indicated above, the endothermic catalytic reactor apparatus and methods described herein can be used to provide numerous products as described above.

Whereas particular embodiments of this invention have been described above for purposes of illustration, it will be evident to those skilled in the art that numerous variations of the details of the present disclosure may be made without departing from the invention as defined in the appended claims.

I claim:

1. An endothermic catalytic reactor apparatus comprising:
a radiant furnace comprising a burner adapted to provide thermal energy to the furnace;
a reactor, having an entrance portion and an exit portion, situated within the furnace and adapted to receive radiant thermal energy from the furnace;
one or more static helical spirals positioned within the reactor so that a material can follow a defined path to travel from the entrance portion to the exit portion, wherein the helical spirals are adapted to hold a catalyst on an outer surface thereof so as not impede the defined flow path;
one or more incoming ports on the entrance portion, adapted to receive reactive starting materials; and
an exit port on or near the exit portion, adapted to expel product from the reactor;
wherein the reactor is adapted to allow the starting materials to receive radiant thermal energy and interact with the catalyst sufficiently to cause a reaction to occur that converts starting materials to product.

2. The endothermic catalytic reactor apparatus according to claim 1, wherein the starting materials are gaseous and flow along the defined path such that the starting materials have a Reynolds number of from 1,000,000 to 15,000,000.

3. The endothermic catalytic reactor apparatus according to claim 1, wherein the starting materials are gaseous and flow along the defined path such that the starting materials have a Nusselt number of from 3,000 to 15,000.

4. The endothermic catalytic reactor apparatus according to claim 1, wherein the starting materials pass through a heat exchanger prior to entering the reactor and enter the reactor at a temperature of from 225° C. to 725° C.

5. The endothermic catalytic reactor apparatus according to claim 1, wherein the starting materials have a mass flow rate through the reactor of from 20 kg/sec to 150 kg/sec.

6. The endothermic catalytic reactor apparatus according to claim 1, wherein the starting materials have a volumetric flow rate through the reactor of from 500 l/sec to 1,000 l/sec.

7. The endothermic catalytic reactor apparatus according to claim 1, wherein the starting materials have a linear velocity through the reactor of from 15 m/sec to 35 m/sec.

8. The endothermic catalytic reactor apparatus according to claim 1, wherein the radiant furnace has a temperature of from 350° C. to 900° C.

9. The endothermic catalytic reactor apparatus according to claim 1, wherein the conversion of starting materials to product is at least 10%.

10. The endothermic catalytic reactor apparatus according to claim 1, wherein the starting materials and product are in their vapor phase when in the reactor.

11. The endothermic catalytic reactor apparatus according to claim 1, wherein the product is separated from non-product materials.

12. The endothermic catalytic reactor apparatus according to claim 11, wherein the non-product materials comprise flammable materials that are combusted in the burner.

13. A method of converting reactants to product comprising:
passing reactants through a heat exchanger to provide heated reactants at a temperature of from 225° C. to 725° C.,
providing heated reactants to an endothermic catalytic reactor apparatus that comprises:
a radiant furnace comprising a burner adapted to provide thermal energy to the furnace;
a reactor, having an entrance portion and an exit portion, situated within the furnace and adapted to receive radiant thermal energy from the furnace;
one or more static helical spirals positioned within the reactor so that a material can follow a defined path to travel from the entrance portion to the exit portion, wherein the helical spirals are adapted to hold a catalyst on an outer surface thereof;
one or more incoming ports on the entrance portion, adapted to receive the reactants; and
an exit port on or near the exit portion, adapted to expel product from the reactor;
wherein the reactor is adapted to allow the reactants to receive radiant thermal energy and interact with the catalyst sufficiently to cause a reaction to occur that converts reactants to a product; and
separating the product from non-product materials;
wherein the reactants have a mass flow rate through the reactor of from 20 kg/sec to 150 kg/sec.

14. The method according to claim 13, wherein the reactants are gaseous and flow along the defined path such that the reactants have a Reynolds number of from 1,000,000 to 15,000,000.

15. The method according to claim 13, wherein the reactants are gaseous and flow along the defined path such that the reactants have a Nusselt number of from 3,000 to 15,000.

16. A method of producing styrene comprising:
passing a reactant stream comprising ethyl benzene through a heat exchanger to provide a heated reactant stream at a temperature of from 450° C. to 725° C.;
providing the reactant stream to an endothermic catalytic reactor apparatus that comprises:
a radiant furnace comprising a burner adapted to provide thermal energy to the furnace;
a reactor, having an entrance portion and an exit portion, situated within the furnace and adapted to receive radiant thermal energy from the furnace;
one or more static helical spirals comprising a defined path positioned within the reactor so that a material can follow the defined path to travel from the entrance portion to the exit portion, wherein the helical spirals are adapted to hold a catalyst on an outer surface thereof;
one or more incoming ports on the entrance portion, adapted to receive the heated reactant stream; and
an exit port on or near the exit portion, adapted to expel a product stream comprising styrene from the reactor;
wherein the reactor is adapted to allow the heated reactant stream to receive radiant thermal energy and interact with the catalyst sufficiently to cause a reaction to occur that converts ethyl benzene to styrene and byproduct hydrogen;

wherein the product stream comprises styrene, hydrogen and optionally unreacted ethyl benzene;

separating the product stream into a primarily aqueous phase, a primarily organic phase and a non-condensable overhead comprising hydrogen;

separating styrene from the primarily organic phase and optionally the primarily aqueous phase;

wherein the conversion of ethyl benzene to styrene is at least 70%.

17. The method according to claim 16, wherein the heated reactant stream is gaseous and flows along the defined path such that the reactant stream has a Reynolds number of from 1,000,000 to 15,000,000 and has a Nusselt number of from 3,000 to 15,000.

18. The method according to claim 16, wherein the styrene is separated from the product stream.

* * * * *